US010234282B2

(12) United States Patent
Winkelmann et al.

(10) Patent No.: US 10,234,282 B2
(45) Date of Patent: Mar. 19, 2019

(54) METHOD AND SYSTEM FOR DETERMINING THE POSITION OF A RADIATION SOURCE

(71) Applicants: Bruker Nano GmbH, Berlin (DE); University of Strathclyde, Glasgow (GB)

(72) Inventors: Aimo Winkelmann, Berlin (DE); Stefano Vespucci, Glasgow (GB)

(73) Assignees: Brunker Nano GmbH, Berlin (DE); University of Strathclyde, Glasgow (GB)

( * ) Notice: Subject to any disclaimer, the term of this patent is extended or adjusted under 35 U.S.C. 154(b) by 0 days.

(21) Appl. No.: 15/643,344

(22) Filed: Jul. 6, 2017

(65) Prior Publication Data
US 2018/0010909 A1    Jan. 11, 2018

(30) Foreign Application Priority Data
Jul. 7, 2016   (EP) .................................... 16178468

(51) Int. Cl.
*G01N 23/203*   (2006.01)
*G01B 15/00*    (2006.01)
*G01T 1/29*     (2006.01)

(52) U.S. Cl.
CPC .......... *G01B 15/00* (2013.01); *G01N 23/203* (2013.01); *G01T 1/2907* (2013.01); *G01N 2223/501* (2013.01)

(58) Field of Classification Search
CPC ................. G01B 15/10; G01N 23/203; G01N 2223/501; H01J 37/28; G01T 1/2907
See application file for complete search history.

(56) References Cited

U.S. PATENT DOCUMENTS 3,581,090 A    5/1971  Brown
2016/0216219 A1*  7/2016  Wright ............. G01N 23/20058

FOREIGN PATENT DOCUMENTS

EP    2 546 638 A2    1/2013

OTHER PUBLICATIONS

Schulson 'Review Electron channeling patterns in scanning electron microscopy', 1977, Jn of Mat Sci, V. 12, pp. 1071-1087.*

(Continued)

*Primary Examiner* — Eliza Osenbaugh-Stewart
(74) *Attorney, Agent, or Firm* — Lewis Roca Rothgerber Christie LLP (57) ABSTRACT

The present invention refers to a method for determining a position of a divergent radiation source (1), comprising Irradiating a pixel detector (2) with a predetermined intensity distribution of radiation with wavelength λ originated from the radiation source (1), wherein the pixel detector (2) comprises a plurality of pixels with pixel coordinates ($x_i$, $y_i$, $z_i$); Detecting, for each of the plurality of pixels, an intensity of the incident radiation (10); Determining, for each of the plurality of pixels, an incidence direction of the incident radiation using information on an orientation of an internal periodic structure at the pixel and the predetermined intensity distribution, wavelength λ and the detected intensity; and Determining the position ($x_p$, $y_p$, $z_p$) of the radiation source (1) using the pixel coordinates ($x_i$, $y_i$, $z_i$) and the incidence direction for each of the plurality of pixels. The invention further refers to a system, a computer-related product and a sample (8) for performing such method and to the use of a pixel detector (2) for determining a position of a divergent radiation source (1).

16 Claims, 3 Drawing Sheets

(56) References Cited

OTHER PUBLICATIONS

Extended European Search Report for European Patent Application No. 16178468.1 dated Nov. 7, 2016, 8pp.
Biggin, S. et al.; "A General Method for Locating the X-ray Source Point in Kossel Diffraction"; J. Appl. Cryst.; 1977; 10; pp. 376-385.
Joy, David C. et al.; "Electron channeling patterns in the scanning electron microscope"; J. Appl. Phys.; vol. 53; No. 8; Aug. 1982; pp. R81-R122.
Maurice, Claire et al.; "A method for accurate localisation of EBSD pattern centres"; Ultramicroscopy 111; 2011; pp. 140-148.
Venables, J.A. et al.; "Accurate microcrystallography using electron back-scattering patterns"; Philosophical Magazine; 1977; vol. 35; No. 5; pp. 1317-1332.
Vespucci, S. et al.; "Digital direct electron imaging of energy-filtered electron backscatter diffraction patterns"; Physical Review B; 92; 2015; pp. 205301-1-205301-9.
Winkelmann, Aimo et al.; "Many-beam dynamical simulation of electron backscatter diffraction patterns"; Ultramicroscopy; 107; 2007; pp. 414-421.
EPO Office Action dated Jan. 11, 2019 for corresponding EP Application No. 16178468.1 (7 pages).
Vysotski et al. "Channeling of neutral particles and photons in crystals," Sep. 1, 1992 *Sov. Phys. Usp.* 35, pp. 725-746.

\* cited by examiner

METHOD AND SYSTEM FOR DETERMINING THE POSITION OF A RADIATION SOURCE

CROSS-REFERENCE TO RELATED APPLICATION(S)

This application is based upon and claims the benefit of priority of European Patent Application No. 16178468.1, filed on Jul. 7, 2016, the entire contents of which are incorporated herein by reference.

FIELD OF THE INVENTION

The present invention relates to a method and a system for determining the position of a radiation source, particularly for use in crystallographic applications. The invention further relates to the use of a pixel detector for determining the position of a radiation source, a computer readable medium related thereto and a sample for a system according to the present invention.

TECHNOLOGICAL BACKGROUND

The structure of crystalline materials can be analyzed using diffraction methods, wherein suitable waves are coherently scattered by the atoms of the material. The direction-dependent intensity of the scattered radiation is then recorded at different scattering angles. Various information on the crystalline material, such as on the crystal structure, chemical bonds or mechanical strain within the sample, can be derived from the recorded angle-dependent intensity distribution of the diffracted waves of the radiation applied.

Suitable radiation can either be electromagnetic radiation, such as X-rays, or massive particle radiation, such as electron or neutron beams, as long as the wavelength of the radiation is within the magnitude of the lattice constant(s) of the structure(s) to be analyzed. While X-ray crystallography still is one of the most widely used techniques in structure analysis, more and more methods utilizing electron beams for resolving crystal structures are developed, as at least some of these methods can be functionally integrated in electron microscopes.

Diffraction patterns of an analyzed sample are often recorded using photodetectors, either alone or in combination with a scintillation screen. With a two-dimensional detector surface only a two-dimensional projection, e.g. a gnomonic projection, of a diffraction pattern directed from the sample into all three dimensions can be recorded. In order to interpret the recorded projected intensities, it is necessary to know the mathematical parameters of the projection function from the three-dimensional to the two-dimensional space. In case of the gnomonic projection, which projects 3D directions on a sphere to 2D points on a plane, the position of the central point of the projection (i.e. the center of the sphere) needs to be known relative to the projection plane. In measurements of diffracted intensities, this so-called pattern center (PC) can correspond to a sample region onto which an incident probe beam is directed and from which the diffracted radiation is emitted into all directions and collected on a planar screen.

In electron backscatter diffraction (EBSD) a crystalline sample is placed in a scanning electron microscope (SEM) and irradiated with a focused electron beam. At least part of the electrons are scattered within the sample and then exit it with an angle-dependent intensity distribution. Using a two-dimensional detector, Kikuchi patterns can be recorded in a gnomonic projection on the detector surface. The backscattering of the incident electrons takes place within a limited region near the incident electron beam position. The position of this source region of the diffraction pattern with respect to the detector surface is the so-called pattern center (PC).

Maurice et al. disclosed a moving screen method for accurate localization of the pattern center of diffraction patterns in EBSD. Therein two diffraction patterns are obtained with two relative positions of detector screen and sample and are thus optically zoomed relative to each other. One of the patterns is then virtually zoomed, i.e. the projection center coordinates are varied, until the cross-correlation with the other pattern reaches a maximum. By comparison of the virtually zoomed and the optically zoomed pattern, a shift value for determining the pattern center relative to the image center can be obtained (C. Maurice, K. Dzieciol, R. Fortunier, Ultramicroscopy) 111, 140 (2011)).

Biggin and Dingley disclosed a method for locating a source point of X-rays in a Kossel diffraction method that shall be applicable to any point-source method, where a pattern center is required. According to the method, spherical balls of steel are placed between the sample and the detector during an otherwise normal recording of a Kossel diffraction pattern. The balls block the radiation from the X-ray source, and thus cast shadows that form ellipses with major axes intersecting at the pattern center (S. Biggin, D. J. Dingley, J Appl Crystallogr 10, 376 (1977)).

The known methods are each prone to a variety of systematic errors and cannot be easily introduced in a standard SEM that is designed for multiple uses. The accuracy in determining the pattern center usually converges at around 0.5 to 1% of the pattern width. The objective of the present invention is to avoid or at least reduce one or more drawbacks of the prior and to provide a method for localizing a radiation source with improved accuracy that can be easily integrated in various structure analysis apparatuses.

SUMMARY OF INVENTION

According to the present invention the objective is solved by a method for determining a position of a divergent radiation source, comprising at least the steps of: Irradiating a pixel detector with a predetermined intensity distribution of radiation with wavelength $\lambda$ originated from the radiation source, wherein the pixel detector comprises a plurality of pixels with pixel coordinates $(x_i, y_i, z_i)$; Detecting, for each of the plurality of pixels, an intensity of the incident radiation; Determining, for each of the plurality of pixels, an incidence direction of the incident radiation using information on an orientation of a periodic structure, preferably a crystal orientation, at the pixel and on the predetermined intensity distribution at the pixel, wavelength $\lambda$ and the detected intensity at the pixel; and Determining the position $(x_p, y_p, z_p)$ of the radiation source using the pixel coordinates $(x_i, y_i, z_i)$ and the incidence direction for each of the plurality of pixels.

In other words, the present invention provides a method for determining the three-dimensional coordinates of a radiation source emitting radiation with wavelength $\lambda$ (in other words divergent waves) that is measured with a pixel detector in form of a two-dimensional intensity distribution or intensity pattern. The pixel detector used in the method according to the invention comprises a detector area that is either planar or curved and comprises a plurality of pixels with pixel coordinates $(x_i, y_i)$ or $(x_i, y_i, z_i)$, respectively. Further, the detector comprises a periodic structure (e.g. a crystalline structure) that is fixed at least within each pixel of the plurality of pixels. The term periodic structure herein denotes a structure that is spatially repeating with a repeat unit in the order of the wavelength of the waves emitted from the localized radiation source of divergent waves. Preferably, the periodic structure is a three-dimensional periodic structure. The method according to the invention is based on the finding, that due to the fixed internal periodic structure of the pixels, the detector comprises a sensitivity in detecting incident radiation of wavelength $\lambda$ that depends on the incidence direction of the radiation on each area element dA and thus on each pixel of the detector. Although the position of a radiation source can be determined in the present invention, it is the wave character of the radiation emitted by that source that allows to determine the incident direction of the radiation.

As a consequence, a predetermined intensity distribution, i.e. a known distribution or a reliably estimated distribution, irradiated on the pixel detector produces a detected intensity pattern, i.e. an intensity value for each of the plurality of pixels, that is not a homogenous transformation of the incident intensity for all of the pixels, but is additionally modulated based on the incidence direction and on the wavelength of the incident radiation. Thus, by using information on the crystalline structure at a pixel, information on the predetermined intensity distribution at the pixel, the detected intensity at the pixel and wavelength $\lambda$ it is possible to reversely determine the incidence direction of the incident radiation. Therefore information on the physical effects underlying the modulation can be used in determining the incidence direction from the aforementioned data. By using, for the plurality of pixels, the pixel coordinates $(x_i, y_i)$ or $(x_i, y_i, z_i)$ together with the determined incidence direction it is possible to determine a position of the radiation source using a triangulation process.

In the context of the present application the information on an orientation of a periodic structure at each of the pixels preferably refer to information on the type of periodic structure, on characteristic distances of that structure and/or on the orientation of that structure relative to a sensor surface of the pixel detector, i.e. a surface formed by a plurality of the pixels. In the preferred case that the periodic internal structure is a crystal structure, the information on an orientation of a periodic structure preferably refer to information on the type of crystal lattice, the lattice constant(s) of this crystal lattice and/or the orientation of the lattice relative to a sensor surface of the pixel detector, e.g. in form of a set of Euler angles. The information on the predetermined intensity distribution at the pixel refer to the actual intensity that can be assumed on each of the pixel and at least to a contrast behavior of that distribution, e.g. whether the distribution can be assumed to be constant at each pixel. The information on the predetermined intensity can be determined as an average of the intensities detected at each of the pixels. The wavelength $\lambda$ is usually known or can be determined in a known fashion otherwise. The information on the detected intensity at the pixel basically is the detected intensity at the pixel that can be electronically reprocessed, e.g. filtered and/or amplified.

The wavelength of the radiation emitted from the radiation source determines the necessary parameters of the periodic structure, e.g. crystalline structure, in the detector pixel. For crystallographic applications, electron, neutron or X-ray waves with wavelengths in the order of typical lattice parameters are needed (e.g. $10^{-10}$ m or less). Preferably, the pixels thus comprise a crystalline material. A different example would be a source of acoustic pressure waves with corresponding wavelengths and internal pixel structure in the order of 1 mm to 1 m. Such structures could be realized with gratings or the like. Further examples would be electromagnetic sources of microwaves, terahertz radiation, infrared, visible, ultraviolet light which would require corresponding periodic structures ("metamaterials") for implementation as the detector type disclosed here. The extension of the resulting detectors would need to be scaled depending on the size of the required resolution of the source coordinates.

In the method according to the present invention, the detected intensity at each of the plurality of pixels depends on the incident intensity at the pixel, the orientation of the periodic structure at the pixel and wavelength $\lambda$. For the example of an incident electron beam, the underlying effect is related to electron channeling and provides, for each pixel, the relationship between incident intensity, detected intensity, the angle between the incident radiation and the orientation of the periodic structure, e.g. a crystal lattice. In short, the probability of an electron being backscattered depends on how close it approaches the scattering atom. In a crystalline material, an incident plane-wave beam will be transformed into a set of standing waves which will vary with the incidence direction of the beam relative to the crystal lattice. Exemplarily, for an electron beam irradiating the crystal lattice in a direction near the Bragg angle for a lattice plane, standing waves will have maxima on the lattice planes or between them. For the case when the multiple Bragg-reflections causes standing waves with maxima between the atomic planes, the backscattering will be reduced, and the incident electrons can penetrate deeper into the crystal. In a simple way, the density of scattering centers experienced by the electron differs with the angle of the electron relative to the crystal lattice planes, e.g. this is characteristically varying for an electron beam with an incidence direction that is near the Bragg angle of a crystal lattice plane.

In the method according to the present invention a detector channeling pattern (DCP) produced inherently within the detector itself is recorded instead of an electron channeling pattern (ECP) for a sample diffracting an incident radiation. The detector channeling pattern is utilized to determine a position of the radiation source. In short, the intensity that is detected at a certain pixel increases as the probability of the incident radiation to be backscattered decreases. Essentially, incident radiation with a lower backscattering probability travels longer distances in the detector material and thus, the probability of contributing to a detectable signal, e.g. by producing an electron hole pair, is increased. The detector channeling pattern thus modulates the detected intensity pattern, consisting of the intensities detected at each of the plurality of pixels. Thereby the detected intensity pattern shows features that are basically related to the Bragg angles for the lattice planes of the periodic structure, e.g. crystalline structure, of the detector. A detailed discussion of the physical effects underlying electron channeling and detector channeling as well as mathematical relationships that can be used to determine the incidence direction using information on an crystal orientation of a periodic structure, preferably a crystal orientation, at the pixel and on the predetermined intensity distribution at the pixel, wavelength $\lambda$ and the detected intensity at the pixel can be found in D. C. Joy et al. *J. Appl. Phys.* 53 R 81 (1982). Without being bound to any theory, the whole content of the latter is incorporated herewith by reference.

With the method according to the present invention the position of a source of divergent waves, i.e. radiation with a wavelength $\lambda$, can be determined solely from the radiation emitted from the source itself. The position determined in the method of the invention can then be used for various purposes. The determined position can be used for calibrating the angular positions in a diffraction pattern from its projection on the pixel detector, i.e. of a detector surface of the pixel detector that is formed of a plurality of pixels. In general the determined position of the radiation source, i.e. its position relative to the pixel detector, can be used as the central point of a projection of 3D directions on a sphere to 2D points on a plane in order to derive the original 3D directions from measured 2D points, i.e. measured intensities.

However, the determination of the position itself could be the final step of the method according to the invention. Then the method is a triangulation method and could be used e.g. to localize satellites, astronomic objects, atoms, molecules, quantum objects, sources of hazardous radiation or others. If the radiation source is a sample, i.e. an object reflecting or deflecting an incident primary radiation, the determined position can be used to determine the topography of that object. Other applications of the position determination method disclosed herein are possible.

In a preferred embodiment, the method according to the present invention further comprises the step: determining, for each of the plurality of pixels, a polar component $\varphi_i$ and/or an azimuthal component $\theta_i$ of an angle of incidence of the incident radiation using the information on a orientation of the periodic structure at the pixel and on the predetermined intensity distribution at the pixel, wavelength $\lambda$ and the detected intensity at the pixel. In a pixel detector comprising a periodic structure, preferably a crystal material, with lattice planes that are oriented plane-parallel to the detector surface the incident intensity is solely modulated in dependence of the polar component $\varphi_i$ of the angle of incidence of the incident radiation. For a pixel detector comprising a periodic structure, preferably a crystalline material, with (lattice) planes that are tilted with respect to the detector surface the incident intensity is modulated in dependence of both a polar component $\varphi_i$ and an azimuthal component $\theta_i$ of an angle of incidence of the incident radiation. Thus, by using information on the incident intensity distribution, the modulated detected intensity distribution, the wavelength $\lambda$ and the orientation of the periodic structure, preferably the crystal orientation, for each pixel of the plurality of pixels, respectively, it is possible to determine the polar component $\varphi_i$ and/or an azimuth component $\theta_i$ of an angle of incidence of the incident radiation.

In a further preferred embodiment, the method according to the present invention comprises the steps: determining, for each of the plurality of pixels, an orientation of the periodic structure, preferably a crystal orientation, by comparing the detected intensity with a simulated intensity, wherein the simulated intensity depends on an assumed orientation of the periodic structure, e.g. an assumed crystal orientation, and an assumed radiation source position and by further determining, for each of the plurality of pixels, an incidence direction of the incident radiation using the determined orientation of the periodic structure at the pixel, the information on the predetermined intensity distribution, wavelength $\lambda$ and the detected intensity. According to this embodiment, the determination of the incidence direction is a two-step process comprising an initial calibration with respect to the orientation of the periodic structure, e.g. the crystal orientation, at the pixels of the detector and the determination of the source position in dependence of the calibrated orientation of the periodic structure.

The calibration procedure preferably involves the quantitative comparison of at least one, preferably multiple, detected intensity patterns (DCP) with theoretical simulations of a detected intensity pattern, wherein the simulations depend on assumed radiation source positions and assumed internal orientations of a periodic structure, e.g. an internal orientation of a crystal structure with respect to the detector surface. For an electron beam as incident radiation, the simulations are preferably conducted using a many-beam dynamical simulation based on the Bloch wave theory of electron diffraction. A further definition of the theory underlying a suitable simulation and mathematical description of such simulation can be found in A. Winkelmann et al. *Ultramicroscopy* 107, 414 (2007). Without being bound to any theory, the whole content of the latter is incorporated herewith by reference.

In the preferred embodiment of the method according to the present invention, the assumed orientation of the periodic structure at each of the plurality of pixels preferably corresponds to manufacturer specifications of the orientation of a crystalline detector material. Exemplarily for a detector comprising a detector surface from a silicon wafer cut in (111) orientation, the assumed crystal orientation is based on this manufacturer specification. Alternatively, the simulations for the detected intensity patterns are solely based on the assumption of a fixed but unknown orientation of the internal periodic structure of the detector, particularly for single-crystalline detector volumes. The so produced simulations for detected intensity patterns are compared to the detected intensity patterns obtained in the calibration process and are varied until the cross-correlation coefficient between measured and simulated patterns reaches a maximum. From the simulated pattern for detected intensities that fits best to the obtained detected pattern, the assumed orientation of the internal periodic structure of the detector, e.g. a crystal orientation as a set of Euler angles, is obtained and set as the determined orientation of the periodic structure at the pixel. Advantageously the so determined orientation of the periodic structure for each of the plurality of pixels considers manufacturing uncertainties.

Alternatively, the calibration procedure is skipped in the method according to the present invention and the information on the orientation of the periodic structure for each of the plurality of pixels is provided by the manufacturer or is determined in an individual measurement. The fixed orientation of the periodic internal structure, e.g. the crystal orientation, of the detector pixels can be independently determined by X-ray diffraction using a suitable goniometer. In principle any measurement technique providing accurate information on this orientation can be used. As the orientation of the periodic structure at the detector pixels is fixed for the lifetime of the detector it is the same for all subsequent experiments using this detector. In other words, the information on the periodic structure provided by the manufacturer or determined in an independent measurement is used as determined orientation of the periodic structure in following measurements and determinations of the incidence direction.

The orientation of the periodic structure that was determined in the calibration is used in following simulations for detected intensity patterns in order to determine that radiation source position according to the method of the present invention. In these simulations solely the radiation source position is varied until in the comparison of the simulated and obtained detected intensity patterns yields a maximum cross-correlation coefficient. From the simulated pattern of the detected intensities that fits best to the actual detected intensity pattern, the radiation source position is obtained. Obviously, the optimization of a cross-correlation coefficient can be exchanged with another image fitting algorithm that achieves similar results, i.e. that is capable of optimizing a numerical value for the similarity of two images.

Further preferred in the method according to the present invention, the radiation source is a quasi-isotropically emitting radiation source with a spatial extension that is small compared to the dimensions of the detector. Preferably the source is well approximated as a point source. The quasi-isotropically emitting radiation source emits radiation, either electromagnetic or particle waves, which is spatially slowly changing within a predetermined solid angle and which can be thus separated from the intensity variations due to the internal detector diffraction. In other words, the intensity variations due to the internal structure of a quasi-isotropically emitting radiation source are small in the solid angles covered by the diffraction features, e.g. Kikuchi bands in the detector channeling pattern. As the source is small compared to the dimensions of the detector, blurring of diffraction features, e.g. as for multiple projection centers, is minimized.

For a radiation source well approximated as a point source and with a sufficient distance from a detector surface of the pixel detector approximately planar wave fronts of radiations are incident on the detector surface and thus, the incident intensity distribution is equal for each of the plurality of pixels. Consequently, each modulation of, or each contrast in, the detected intensity pattern is solely provided by detector channeling as described above. Advantageously in this embodiment, the information that the predetermined intensity distribution is isotropic, i.e. equal for each of the plurality of pixels, is sufficient in determining the incidence direction for the incident direction, i.e. for the simulations as described above.

In an alternative embodiment of the method according to the present invention, the predetermined intensity distribution incident on the detector surface is non-isotropic. In this embodiment, the information on the predetermined intensity distribution must be more detailed and must at least contain contrast information for the incident intensity pattern on the detector surface due to the predetermined intensity distribution. In other words, at least the relative incident intensities of the plurality of pixels, i.e. the ratio of incident intensities of two of the plurality of pixels at a time, must be known. By this, the modulation due to the angle-dependent detector channeling as described above can be clearly derived by using the information on the predetermined intensity distribution and the detected intensity distribution.

In a further preferred embodiment of the method according to the present invention, the pixel detector comprises a detector surface, divided into a plurality of pixels with pixel coordinates $(x_i, y_i, z_i)$, and a detector volume, divided into a plurality of voxels corresponding to the plurality of pixels, wherein each voxel comprises an internal periodic structure as described above. Preferably each voxel comprises a crystalline material with fixed crystal orientation. The orientation of the periodic structure can vary between different pixels or between different groups of pixels of the detector, as long as the orientation of the periodic structure within a volume of or corresponding to a single pixel, e.g. a voxel, is fixed. Different orientations of the internal periodic structure of different pixels must be then considered in the simulations of detected intensity patterns for the calibration procedure as described above. In such case in the calibration procedure described above orientations of several internal periodic structures, i.e. orientation of several crystal structures relative to the detector surface, are determined either for individual pixels or for groups of pixels. In the simulation of detected intensity patterns with varying radiation source position for determining this position, the several determined orientations of periodic structures are then set as orientations for the respective pixels.

Further preferred, the pixel detector comprises a detector surface, divided into a plurality of pixels with pixel coordinates $(x_i, y_i, z_i)$, and a detector volume, divided into a plurality of voxels corresponding to the plurality of pixels and comprising a single periodic structure, preferably a single crystalline material. Thus, in this embodiment, the orientation of the internal periodic structure is equal for all voxels and thus at all pixels. Thus, the modulation of the incident intensity distribution is solely dependent on the incidence direction for each of the plurality of pixels. Thus, in the calibration procedure it is sufficient to set the orientation of the periodic internal structure to be fixed and equal for all pixels despite being unknown in order to find the determined orientation of the periodic internal structure. Further, in the determination of the incidence direction for each of the plurality of pixels it is sufficient to set the orientation of the periodic internal structure to be fixed and equal for all pixels despite being unknown in order to determine the radiation source position.

In the context of the present invention, a voxel is a subvolume of a sensitive detector volume, wherein one surface of the voxel constitutes a pixel on the detector surface of the detector. The predetermined intensity distribution is incident on the detector surface and the plurality of pixels and enters through the surface into a plurality of voxels corresponding to the latter. Within the voxels, the radiation, i.e. electromagnetic waves, particle waves from neutrons or electrons, or other waves, is diffracted based on its propagation direction relative to the internal periodic structure of the voxel, e.g. relative to the orientation of crystal lattice planes. The less probable it is for the radiation to be backscattered, the longer the radiation interacts with the detector material, generating more electron-hole pairs and thus, the stronger is the detected intensity.

In a further preferred embodiment of the method according to the present invention, the divergent radiation source is a sample region reflecting an incident beam of a primary radiation. In other words, a beam of a primary radiation is directed onto a region of a sample and is reflected or deflected by this sample region. The deflection or reflection of the primary radiation, either electromagnetic or particle waves, can be due to an variety of processes, comprising scattering, diffraction, refraction excitation of auger electrons, excitation of photons and/or excitation of collective solid state phenomena. In other words the sample region is a divergent radiation source for the reflected or deflected primary radiation. In the context of this application, the reflected or deflected primary radiation is also referred to as secondary radiation. In this embodiment, the present method can be utilized in determining the projection center in a diffraction method. Exemplarily the method can be utilized to determine the projection center of detected Kikuchi patterns in EBSD.

Further preferred in this embodiment, the sample region comprises a polycrystalline or amorphous sample volume that is configured for quasi-isotropically reflecting or deflecting the primary radiation. The secondary radiation constitutes the predetermined intensity distribution irradiating the detector surface is thus a quasi-isotropic intensity distribution in this embodiment. This provides the advantages as described above, e.g. the modulation of the detected intensity distribution is solely due to detector channeling as described above. Alternatively, the sample region comprises a crystalline or polycrystalline sample volume that is configured for anisotropically reflecting or deflecting the primary radiation. The secondary radiation then constitutes an anisotropic predetermined intensity distribution irradiating the detector surface. Thus, the detected intensity pattern comprises an intensity modulation due to the detector channeling that is overlapped with an intensity modulation due to the reflection or deflection of the primary radiation in the sample region, e.g. with Kikuchi or Kossel lines. Preferably image-processing techniques are used to identify the contribution of the detector channeling modulation and by the modulation due to the sample. Suitable image-processing techniques, e.g. template-matching and related approaches, are described in Bovik, "Handbook of Image and Video Processing" Chapter: "9.5 Watermarking Techniques for Image Authentication and Copyright protection". The latter is incorporated herewith by reference in full extent. Advantageously the detected intensity is increased as the probability of backscattering is decreased as described above. Thus, often the both aforementioned modulations will have converse effects on the measured intensities and contrast between modulations is high.

Another aspect of the present invention relates to a system for determining the position of a divergent radiation source, the system comprising: a divergent radiation source; a pixel detector with a plurality of pixels with pixel coordinates ($x_i$, $y_i$, $z_i$); and a control unit configured for performing a method as described above. Particularly preferred, the system according to the present invention is integrated in an X-ray diffractometer or in an electron microscope, such as a TEM, SEM, REM or STEM. Particularly preferred the system according to the present invention is integrated in a SEM designed for multiple uses and/or the radiation source is a sample region configured for deflecting or reflecting the primary electron beam.

In a preferred embodiment of the system according to the present invention, the pixel detector is a hybrid pixel detector, comprising a sensor with a detector surface, divided into a plurality of pixels with pixel coordinates ($x_i$, $y_i$, $z_i$), and a detector volume, divided into a plurality of voxels corresponding to the plurality of pixels, wherein each voxel comprises a material with a fixed orientation of an internal periodic structure, preferably a crystalline material with fixed crystal orientation, and an electronics chip with a plurality of amplification pixels, each corresponding to one of the plurality of pixels of the sensor. Particularly preferred the pixel detector is a digital CMOS hybrid pixel detector as described in S. Vespucci et al. *Phys. Rev. B* 92, 205301 (2015). The whole content of the latter is incorporated herewith by reference.

In a further preferred embodiment of the system according to the present invention, the system according to the present invention comprises a primary radiation source. The divergent radiation source is preferably constituted by a calibration region of a sample, wherein the calibration region comprises a polycrystalline or amorphous material and wherein the calibration region is configured to quasi-isotropically reflect or deflect an incident beam of primary radiation. Preferably in this embodiment, the system is integrated in an apparatus configured for crystallographic studies on the sample. In such an apparatus the samples is irradiated by a primary beam that is diffracted by the sample in an angle-dependent manner such that an intensity distribution recorded over a solid angle comprises information on the inner structure of the sample. In order to utilize the additional functionality added to the apparatus by the system according to the invention a specially prepared sample is provided.

Another aspect of the present invention relates to a sample for an apparatus configured for crystallographic studies, the sample comprising at least one calibration region with a polycrystalline or amorphous material that is configured to quasi-isotropically reflect or deflect an incident beam of primary radiation. The sample might further comprise other regions optimized for standard structure analysis in the apparatus. The calibration region of the sample provides that a primary radiation directed to this region generates a quasi-isotropic intensity distribution incident on the pixel detector with the advantages for the method according to the invention as described above. By using the sample according to the invention the position of the radiation source is determined with high precision and the interpretation of the recorded intensities in the standard structure analysis is improved.

In a preferred embodiment the sample comprises structure analysis regions, configured, e.g. prepared, for being analyzed in a structure analysis apparatus, e.g. an X-ray diffractometer or a SEM, and further comprises calibration regions. The calibration regions preferably comprise a layer of a polycrystalline, preferably nanocrystalline, material that can be considered amorphous for the standard structure analysis method utilized in the structure analysis apparatus. Exemplarily the layer comprises a thickness of less than 100 nm, less than 50 nm or preferably less than 10 nm and further preferred the layer comprises $HfO_2$. By varying the thickness of this layer covering the calibration region, the detected intensity modulated by the detector channeling as described above can be increased with respect to a detected intensity modulation due to diffraction of the primary radiation in the sample.

Another aspect of the present invention relates to computer-readable medium comprising program instructions, wherein when executed in a control unit of a system as described above the program instructions are operable to perform a method as described above.

Another aspect of the present invention relates to the use of a pixel detector for determining a position of a divergent radiation source, wherein the pixel detector comprises a detector surface, divided into a plurality of pixels with pixel coordinates ($x_i$, $y_i$, $z_i$), and a detector volume, divided into a plurality of voxels corresponding to the plurality of pixels, wherein each voxel comprises a material with a fixed orientation of an internal periodic structure, preferably a crystalline material with a fixed crystal orientation, at each of the plurality of voxels, wherein the pixel detector is irradiated with radiation originated from the radiation source; wherein the radiation has a predetermined intensity distribution and a wavelength $\lambda$ and wherein an intensity of the incident radiation is detected for each of the plurality of pixels, wherein for each of the plurality of pixels an incidence direction of the incident radiation is determined using information on the orientation of the internal periodic structure at the pixel and the predetermined intensity distribution at the pixel, wavelength $\lambda$ and the detected intensity at the pixel, and wherein the position ($x_p$, $y_p$, $z_p$) of the radiation source is determined using the pixel coordinates ($x_i$, $y_i$, $z_i$) and the incidence direction for each of the plurality of pixels. By such use of a pixel detector the advantages as described with respect to the method according to the present invention can be achieved with any apparatus, e.g. a structure analysis apparatus, comprising a divergent radiation source and a suitable pixel detector. Preferably the determined position is used to determine a three dimensional pattern from its two dimensional projection onto the pixel detector, i.e. onto the detector surface of the pixel detector that is formed by a plurality of pixels.

Further aspects and preferred embodiments of the present invention result from the dependent claims, the drawings and the following description of the drawings. Different disclosed embodiments are advantageously combined with each other if not stated otherwise.

BRIEF DESCRIPTION OF THE DRAWINGS

The features of the invention become apparent to those skilled in the art by the detailed description of exemplary embodiments with reference to the attached drawings in which.

DETAILED DESCRIPTION OF THE INVENTION

Figure 1:
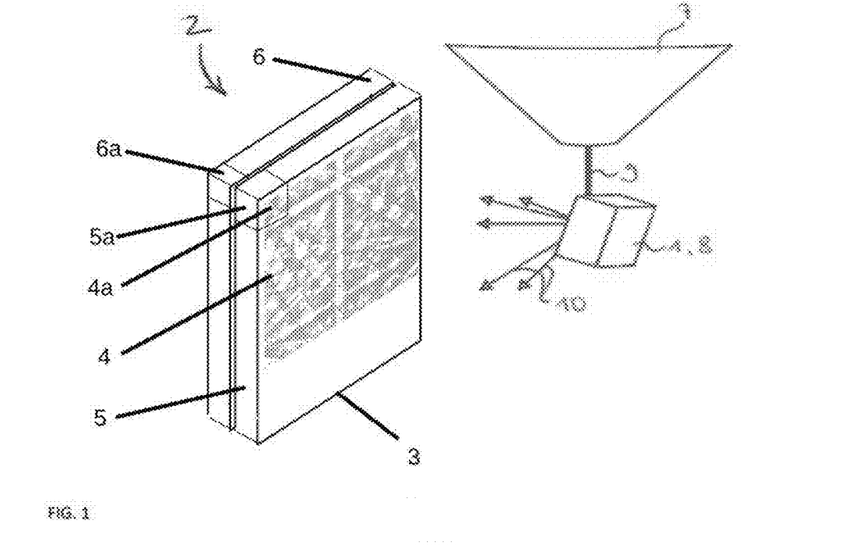
FIG. 1 shows a schematic illustration of a system according to an embodiment.

Referring to FIG. 1, an exemplary embodiment of a system according to the invention is shown, the system being integrated in a scanning electron microscope (SEM) as an apparatus for electron backscatter diffraction. The SEM comprises an electron source 7 as primary radiation source that radiates a sample 8 with a focused electron beam 9 as primary radiation. The electron beam 9 is focused on a region of a sample 8 and is diffracted by the sample in this region. Thereby, the sample region becomes a divergent radiation source 1 for backscattered electrons 10 that are incident on a detector surface 4 of sensor 3.

The backscattered electrons produce a diffraction pattern as a predetermined intensity distribution on the detector surface 4, wherein the intensity can be modulated by sample 8 dependent of the inner structure of the sample. Through the detector surface 4, the electrons enter a detector volume 5, wherein the electrons interact with the detector material in producing electron-hole pairs. The electron hole pairs lead to a current that is detected and amplified by an electronics chip 6 that is affixed to the sensor 3. The sensor 3 and electronics chip 6 together constitute detector 2.

Figure 2:
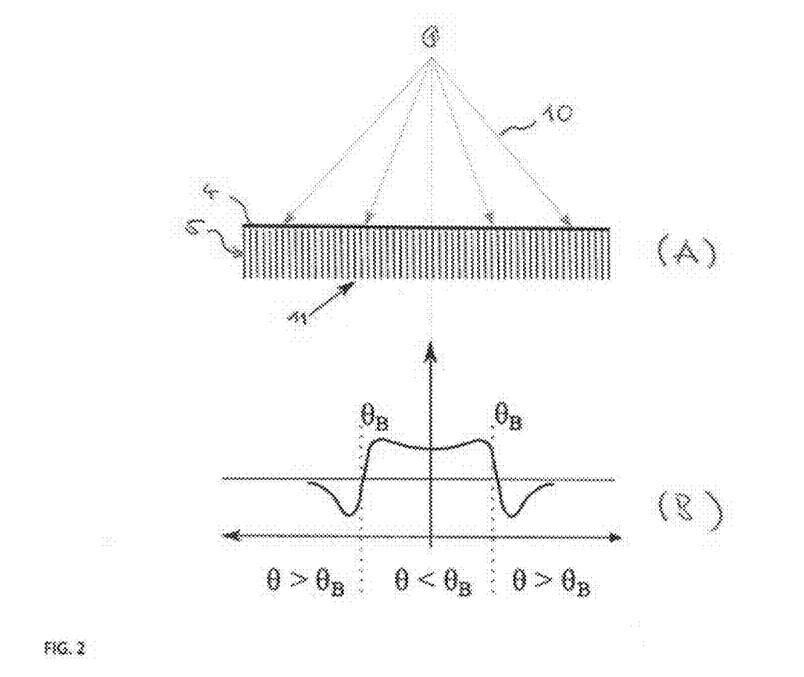
FIG. 2 shows (A) a schematic illustration of a detector channeling effect of electron waves incident on a single crystalline detector and (B) the angular dependence of backscattered intensity.

FIG. 2 (A) shows a schematic illustration of the detector channeling effect that is the physical effect underlying the method according to the invention. The latter effect results e.g. if backscattered electrons 10, as shown in FIG. 1, are irradiated on a detector surface 4, as shown in FIG. 1, comprising a crystalline structure with multiple crystal lattice planes 11.

As shown in FIG. 2 (A), the electrons 10 emitted from the radiation source 1 (in FIG. 1 the spot where the electron beam 9 from the SEM 7 hits the sample 8) travel towards the detector plane 4 that is made from a silicon wafer cut in (111) orientation. The electrons impinge on each pixel 4a of detector surface 4 at a specific incidence direction, e.g. given by the polar component $\varphi_i$ of the angle of incidence of the incident radiation with respect to the surface normal of the detector surface 4 and the azimuth component $\theta_i$ of the angle of incidence of the incident radiation with respect to the surface plane of the detector surface 4.

The penetration depth of the incident radiation 10 into the silicon detector volume 5 is determined by multiple electron reflections at the silicon crystal lattice planes 11 within the detector volume 5 and changes near the Bragg angle, because of the preferential excitation of Bloch waves that are localized either on lattice planes or exactly between them (cf. D. C. Joy et al. *J. Appl. Phys.* 53 R 81 (1982)). Since the incident radiation 10 penetrates to various depth into the detector volume 5, the excitation of electron-hole pairs in the silicon voxel, i.e. the intensity detected at this pixel, is changed as a function of the incidence direction, as shown in FIG. 2. Because the electrons can go less deep when there is a large backscattered signal, the detected intensity pattern modulated by the detector channeling effect is negatively proportional to the backscattered intensity as shown in FIG. 2 (B).

Figure 3:
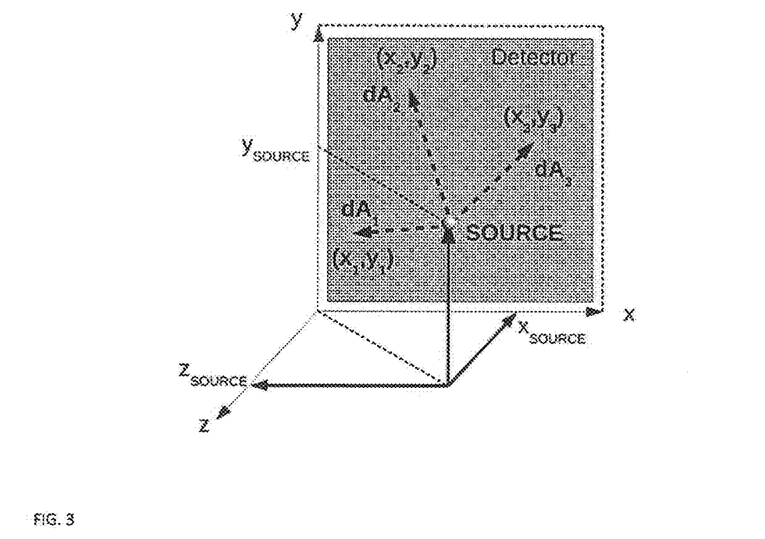
FIG. 3 shows a schematic illustration of the principle of determining the radiation source position according to the present invention.

The detector channeling effect thus provides a one-to-one relationship between pixel position $(x_i, y_i)$ on detector surface 4 and the incidence direction of the incident radiation and thus the radiation source position $(x_{SOURCE}, y_{SOURCE}, z_{SOURCE})$. As shown in FIG. 3, planar detector surface 4 with area elements $dA_n$ is reacting to diffraction effects of incident radiation from the source 1 in the area element $dA_n$. Each area element $dA_n$ at a specific position $(x_n, y_n)$ on the detector is showing an intensity which is related to the direction from the radiation source 1 to the area element $dA_n$ and vice versa. A triangulation procedure involving the intensities from all area elements $dA_n$; i.e. from all pixels, of the detector 2 thus allows to pinpoint the position of source 1.

Figure 4:
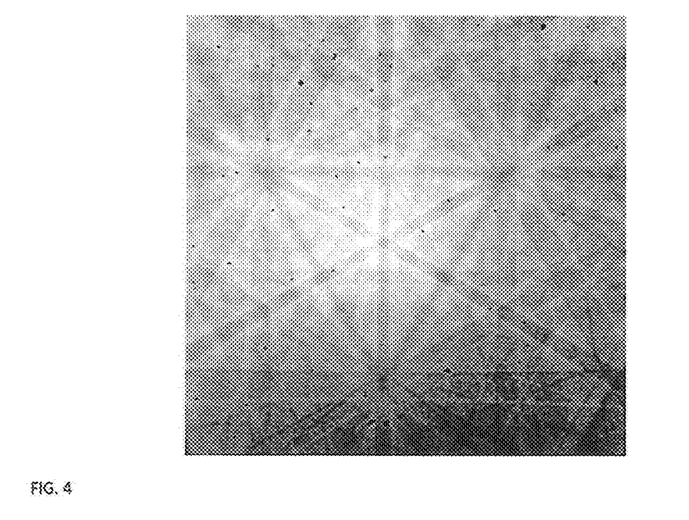
FIG. 4 shows a schematic illustration of detected intensity pattern modulated by a detector channeling pattern (DCP)

An exemplary detected intensity pattern solely modulated by the detector channeling effect, i.e. a pure detector diffraction pattern, is shown in FIG. 4. The shown 2D intensity pattern is visible in the detector response even in total absence of diffraction effects from sample 8. The observed patterns further have the negative intensity distribution relative to what is usually observed for backscattered electrons from a crystal. Thus, these patterns are interpreted as electron channeling patterns formed not by the sample 8 but in the crystalline detector volume 5 instead. A pattern as shown in FIG. 4 will be obtained by detecting an incident radiation from an amorphous sample 8 as divergent radiation source 1 of deflected or reflected primary radiation with a single-crystalline detector made from a silicon wafer cut in (111) orientation.

Crystallographically, the detector channeling pattern gives crystal lattice directions ("zone axes") as crossing points of the center lines of the Kikuchi bands seen in the pattern. The angles between all lattice directions are known for the detector structure used and thus provide the calibration reference values. In order to find the absolute coordinates of the source point mathematically, one can (a) determine the two-dimensional position $(x_i, y_i)$ of the crossing points (zone axes) in the measured pattern image and (b) assign the respective three-dimensional lattice direction $[u_i v_i w_i]$ to each of these points. In addition, from the detector crystal calibration described above, one obtains the three-dimensional crystallographic direction of the fixed detector surface normal direction [$u_N v_N w_N$], while the respective two-dimensional projection point ($x_N$, $y_N$) of this direction is changing in dependence on the actual source point position and needs to be identified in the measured pattern image. Measured in absolute units of the detector coordinate system, this ($x_N$, $y_N$) then directly provides the two-dimensional coordinates of the source point ($X_{SOURCE}$, $Y_{SOURCE}$) because, by definition of the gnomonic projection, the surface normal of the planar detector is going through the source point of the projection. The remaining z-component $Z_{SOURCE}$ of the source point can be obtained by calculating right-angled triangle(s), with the 90° angle between the experimentally measured 2D vector(s) ($x_i-x_N$, $y_i-y_N$) and the surface normal. The 2D vector(s) ($x_i-x_N$, $y_i-y_N$) in the detector plane subtend the known angle(s) $\alpha_i$ between [$u_i v_i w_i$] and [$u_N v_N w_N$] as viewed from the source point. Thus, $Z_{SOURCE}$ is given as the length of the adjacent leg (along [$u_N v_N w_N$]) of the theoretically known angle $\alpha_i$ between [$u_N v_N w_N$] and [$u_i v_i w_i$] at the source point, where the opposite leg is measured experimentally as $d_i=|(x_i-x_N, y_i-y_N)|$, i.e. $Z_{SOURCE}=d_i/\tan(\alpha_i)$. While it appears that a single measurement [$u_i v_i w_i$] and [$u_N v_N w_N$] can be used to roughly estimate $Z_{SOURCE}$, the accuracy of the $Z_{SOURCE}$ value depends on the method used to identify the corresponding ($x_i$, $y_i$) and ($x_N$, $y_N$) in the pattern image. The precision of the method can be estimated from the statistical variation of the values of $z_{SOURCE}$ in dependence on the various measured $d_i$. Alternatively, in order to use the complete information present in the pattern (i.e. beyond identifying discrete point coordinates) and to achieve the highest accuracy, one can apply a quantitative comparison between the complete measured 2D pattern and a simulated pattern with the source point coordinates ($X_{SOURCE}$, $Y_{SOURCE}$, $Z_{SOURCE}$) as parameters like described below. It is stressed again, that in order to identify (directly or implicitly) the direction of the reference zone axes, one needs to measure a 2D information as the collective information of the plurality of pixels relative to each other. The intensity of a single pixel does not suffice to assign a direction to that pixel.

Figure 5:
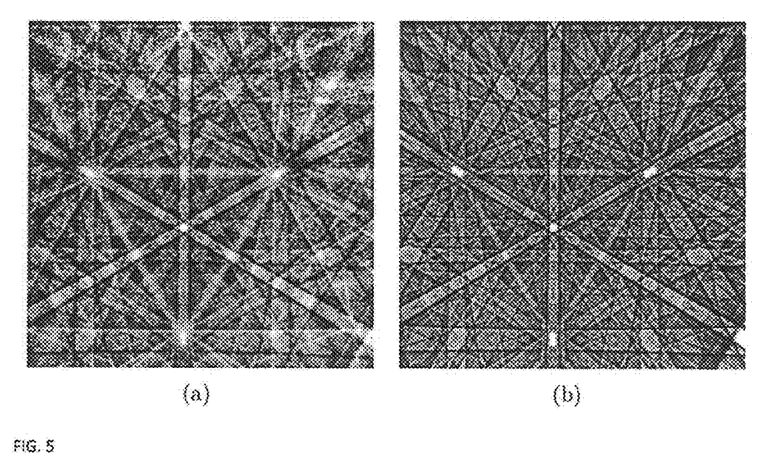
FIG. 5 shows the comparison of the negative of (a) a measured and (b) a simulated detector channeling pattern.

FIG. 5 shows a calibration of the inverted detected intensity pattern (left side) solely modulated by the detector channeling effect by comparison with a simulation for a detected intensity pattern (right side) that was produced using the dynamical theory of electron diffraction (cf. A. Winkelmann et al. *Ultramicroscopy* 107, 414 (2007)). The 3D parameters of the electron source ($X_{SOURCE}$, $Y_{SOURCE}$, $Z_{SOURCE}$) and the internal orientation of the silicon crystal structure with respect to the detector surface plane are input to the simulation and a best-fit optimization procedure gives the 3D parameters of the electron source ($X_{SOURCE}$, $Y_{SOURCE}$, $Z_{SOURCE}$). The internal orientation of the silicon crystal structure relative to the edges of the detector is be described by Euler angles ($\phi_1, \Phi, \phi_2$) that describe a rotation sequence around moving ZXZ-axes in the Bunge convention.

The fixed detector crystal orientation is estimated as the mean orientation determined from a series of measurements which consist in moving the 12 keV electron beam 9 in a regular two-dimensional grid over the surface of a sample 8 that shows no backscattering diffraction pattern. The calibration procedure for each measured pattern involves the quantitative comparison of the measured pattern with theoretical simulations depending on the radiation source 1 position and the internal orientation of the silicon crystal structure with respect to the detector surface 4. In a 10×10 map with approximately 10 µm step size on the sample 8, the best fit orientation was determined by the optimization of the normalized cross-correlation coefficient r relative to simulated Kikuchi data for silicon. For the dynamical electron diffraction simulations and the best-fit optimizations, the software ESPRIT DynamicS by Bruker Nano, Berlin, was applied.

In a first calibration step, both the 3D parameters of the sample 8 as electron source ($X_{SOURCE}$, $Y_{SOURCE}$, $Z_{SOURCE}$) and the internal orientation of the silicon crystal structure in detector volume 5 with respect to the detector surface 4 plane were parameters left to vary in the optimization procedure. As the crystalline detector volume is from a commercial quality silicon wafer cut in (111) orientation, a fixed despite unknown orientation for the crystalline detector volume 5 was assumed in the simulation. Using the software MTEX (cf. F. Bachmann et al. *Solid State Phenom.* 160, 63 (2010)) this fixed orientation was approximated as the mean orientation from all the measurements in the map and resulted in Euler angles of ($\phi_1=179.95°$, $\Phi=54.53°$, $\phi_2=45.15°$,). This corresponds to a misorientation angle of 0.24° away from an ideal (111) surface, which is compatible with the manufacturing uncertainties. In a second determination step, the detector crystal orientation was then fixed in the simulations at the determined mean crystal orientation obtained in the first run in order to obtain the final best-fit radiation source 1 position values. The best-fit coordinates with a cross-correlation coefficient of r=0.71 of the electron source were ($x_P$, $y_P$, $z_P$)=(6313 µm, 5753 µm, 6416 µm) in the coordinate system of FIG. 3.

Figure 6:
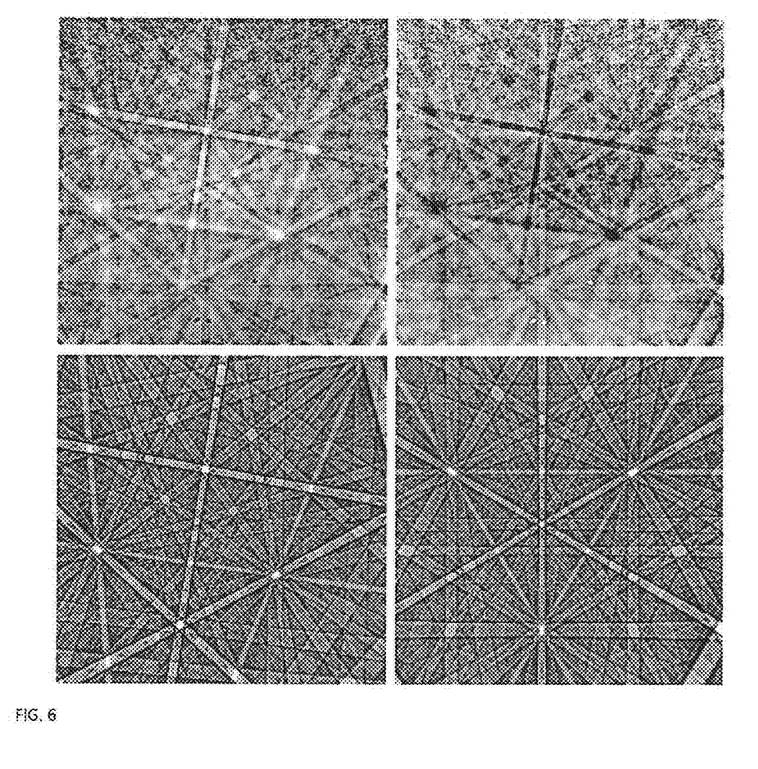
FIG. 6 shows a measured EBSD pattern superimposed with a detector channeling pattern and a simulated EBSD pattern and a simulated detector channeling pattern.

In an alternate embodiment of the method according to the invention, a EBSD pattern superimposed with a detector channeling pattern is measured and used to determined the radiation source position and therewith the sample orientation by comparison with either a simulated EBSD pattern or a simulated detector channeling pattern, as shown in FIG. 6. According to this embodiment, the underlying watermark due to the detector channeling effect is used to calibrate an experimental Kikuchi pattern without using any other information than the pattern itself and the instrumentally fixed crystal orientation of detector volume 5.

Therefore FIG. 6 shows a Kikuchi pattern measurement at 25 keV using a silicon sample covered by 10 nm of nanocrystalline $HfO_2$, which for Kikuchi pattern formation can be considered amorphous. The crystal orientation in the detector volume 5 was assumed at the values of (179.95, 54.53, 45.15) as determined above. The panels in the top row of FIG. 6 show the measured pattern (left) and an inverted copy (right) of that pattern. The lower panel shows on the right side the best-fit simulation for the radiation source 1 position from the negative of the total experimental pattern. The radiation source 1 position, i.e. the projection center, was determined with a best fit r-value of 0.38 at ($x_P$, $y_P$, $z_P$)=(6305 µm, 6888 µm, 6388 µm). This corresponds to viewing angles on the detector screen of 95.2 degrees horizontally and 95.5 degrees vertically.

It is instructive to observe that the cross-correlation approach is stable enough to detect the local minimum of r when the simulated pattern registers with that part of the pattern structure that is connected only to the detector diffraction. Finally, the orientation of the measured sample region is obtained by fitting the original measurement in the top left panels of FIG. 6 assuming the projection center determined in the previous step from the inverted pattern in the top right panel. The result is shown in the bottom left panel of FIG. 6 and corresponds to an orientation of ($\phi_1=179.95°$, $\Phi=19.93°$, $\phi_2=215.59°$). The orientation was determined with a best fit r-value of r=0.43, again showing a selective minimum, but now for the structure corresponding to the sample orientation. In the optimization procedure using two different patterns mixed in one image, it is useful that one pattern is a negative since this should tend to stabilize the optimization procedure that looks for a maximum of the cross-correlation coefficient, in contrast to a minimum that would be reached for the negative pattern.

It could be envisaged to combine both optimizations in a simultaneous fit procedure. In the example experiment related to FIG. 6, the relative mixture of sample 8 and detector volume 5 diffraction was tuned to about 50% each by adjusting the energy of the electron beam 9 and the thickness of the covering $HfO_2$ film. In a conventional experiment involving high-quality crystalline surfaces, the pattern contribution due to the detector channeling effect is on the order of parts of a percent. However, as the detector diffraction contribution is in principle known, the extraction of this contribution from a measured Kikuchi pattern should be possible by image processing techniques like template matching or similar approaches.

The pixel detector used in the method according to the embodiment described above comprises a sensor 3 with a detector surface 4, divided into a plurality of pixels or pixel surfaces 4a with pixel coordinates (xi, yi, zi), and a detector volume 5, divided into a plurality of voxels or pixel volumes 5a corresponding to the plurality of pixels 4a. Each voxel 5a comprises a crystalline material with fixed crystal orientation. The pixel detector further comprises an electronics chip 6 with a plurality of amplification pixels 6a, each corresponding to one of the plurality of pixels 4a.

In the case of the pixel detector 2 used in the exemplarily methods as described above, the sensor 3 and the electronics chip 6 are independent, wherein the sensor 3 comprises 300 μm of silicon. The detector 2 consists of arrays of individual independent counters. Each pixel 4a of the sensor 3 has its own amplification pixel 6a in the electronics chip 6. Sensor 3 and electronics chip 6 are composed of 256×256 square pixels 4a, each 55 μm*55 μm in size, covering a global surface of around 1.4 cm*1.4 cm. Each pixel of the sensor 3 is electrically and mechanically connected, through solder bumps, to the corresponding pixel of the CMOS ASIC electronics chip 6.

Each pixel 6a of the electronics is basically composed of a charge sensitive amplifier, a discriminator, and a 14-bit counter. Each amplification pixel basically 6a comprises a sensor with bias voltage, solder bumps, preamplifier, threshold, discriminator, threshold adjustment and counter. The basic operating principle is as follows: when incident radiation hits a pixel 4a of sensor 3 a cloud of charges (electron-hole pairs) is generated within the material of the sensor 3. The quantity of generated charge is proportional to the total energy deposited within the sensor 3 by the incident radiation. The charges, drifting under the effect of the electric field applied to the sensor 3, are collected by the solder bump and transferred to the ASIC electronic chip 6. The signal from the sensor 3 is amplified by the shaping preamplifier and then compared, by the discriminator, with a threshold value. If the signal is greater than the specified threshold value, the discriminator generates a logic signal whose width is proportional to the time for which the voltage at the output of the preamplifier is above the threshold. The global threshold set for the chip 6 can be adjusted individually for each pixel, in order to compensate for small differences between pixels. An equalization of the matrix is typically performed in order to have a more uniform response within the global detector area. If the threshold level is set above the intrinsic noise of the device, it is possible to operate in noise-free conditions.

REFERENCE SIGNS

1 divergent radiation source
2 pixel detector
3 sensor
4 detector surface
4a pixel surface
5 detector volume
5a pixel volume
6 electronics chip
6a amplification pixel
7 primary radiation source
8 sample
9 primary radiation
10 predetermined intensity distribution/incident radiation/backscattered electrons
11 crystal lattice planes

The invention claimed is:

1. Method for determining a position of a divergent radiation source, comprising:
   irradiating a pixel detector with a predetermined intensity distribution of radiation with wavelength λ originated from the radiation source, wherein the pixel detector comprises a plurality of pixels with pixel coordinates $(x_i, y_i, z_i)$;
   detecting, for each of the plurality of pixels, an intensity of the incident radiation;
   determining, for each of the plurality of pixels, an incidence direction of the incident radiation using information on an orientation of an internal periodic structure within the pixel and the predetermined intensity distribution, wavelength λ and the detected intensity; and
   determining the position $(x_p, y_p, z_p)$ of the radiation source using the pixel coordinates $(x_i, y_i, z_i)$ and the incidence direction for each of the plurality of pixels.

2. Method according to claim 1, further comprising:
   the detected intensity for each of the plurality of pixels depends on the incident intensity distribution and the orientation of the internal periodic structure within the pixel and wavelength λ.

3. Method according to claim 1, further comprising:
   determining, for each of the plurality of pixels, a polar component ($\varphi_i$ and/or an azimuthal component θi of an angle of incidence of the incident radiation using the information on an orientation of an internal periodic structure within the pixel and the predetermined intensity distribution, wavelength λ and the detected intensity.

4. Method according to claim 1, further comprising:
   determining, for each of the plurality of pixels, an orientation of an internal periodic structure by:
   comparing the detected intensity with a simulated intensity, wherein the simulated intensity depends on an assumed orientation of an internal periodic structure and an assumed radiation source position or measuring the orientation of an internal periodic structure in an independent measurement;
   determining, for each of the plurality of pixels, an incidence direction and the position $(x_p, y_p, z_p)$ of the radiation source by:
   comparing the detected intensity with a simulated intensity, wherein the simulated intensity depends on the determined orientation of an internal periodic structure and an assumed radiation source position of the incident radiation.

5. Method according to claim 4, characterized in that:
the assumed orientation of an internal periodic structure within each of the plurality of pixels corresponds to manufacturer specifications on the orientation of an internal periodic structure; and the determined orientation of an internal periodic structure at each of the plurality of pixels considers manufacturing uncertainties.

6. Method according to claim 1, characterized in that:
the radiation source comprises a spatial extension that is small compared to the dimensions of the detector and quasi-isotropically emits radiation in a predetermined solid angle, and the predetermined intensity distribution is isotropic at each of the plurality of pixels.

7. Method according to claim 1, characterized in that:
the pixel detector comprises a detector surface, divided into a plurality of pixels with pixel coordinates ($x_i$, $y_i$, $z_i$), and a detector volume, divided into a plurality of voxels corresponding to the plurality of pixels, wherein each voxel comprises a material with a fixed orientation of an internal periodic structure.

8. Method according to claim 1, characterized in that:
the pixel detector comprises a detector surface, divided into a plurality of pixels with pixel coordinates ($x_i$, $y_i$, $z_i$), and a detector volume, divided into a plurality of voxels corresponding to the plurality of pixels and comprising a single crystalline material.

9. Method according to claim 1, characterized in that:
the divergent radiation source is a sample region reflecting or deflecting an incident beam of a primary radiation.

10. Method according to claim 9, characterized in that:
the sample region comprises a polycrystalline or amorphous material that is configured for quasi-isotropically reflecting or deflecting the primary radiation.

11. System for determining the position of a divergent radiation source, comprising:
a divergent radiation source emitting radiation with wavelength $\lambda$;
a pixel detector with a plurality of pixels with pixel coordinates ($x_i$, $y_i$, $z_i$); and
a control unit configured for performing a method according to claim 1.

12. System according to claim 11, characterized in that:
the pixel detector is hybrid pixel detector, comprising a sensor with a detector surface, divided into a plurality of pixels with pixel coordinates ($x_i$, $y_i$, $z_i$), and a detector volume, divided into a plurality of voxels corresponding to the plurality of pixels, wherein each voxel comprises a material with fixed orientation of an internal periodic structure, and an electronics chip with a plurality of amplification pixels, each corresponding to one of the plurality of pixels.

13. The system according to claim 11, further comprising a primary radiation source,
wherein the divergent radiation source is a calibration region of a sample;
wherein the calibration region comprises a polycrystalline or amorphous material
that is configured for quasi-isotropically reflecting or deflecting an incident beam of primary radiation.

14. A computer readable medium comprising program instructions, wherein when executed in a control unit of a system according to claim 11 the program instructions are operable to perform the method for determining a position of a divergent radiation source, comprising:
irradiating a pixel detector with a predetermined intensity distribution of radiation with wavelength $\lambda$ originated from the radiation source, wherein the pixel detector comprises a plurality of pixels with pixel coordinates ($x_i$, $y_i$, $z_i$);
detecting, for each of the plurality of pixels, an intensity of the incident radiation;
determining, for each of the plurality of pixels, an incidence direction of the incident radiation using information on an orientation of an internal periodic structure within the pixel and the predetermined intensity distribution, wavelength $\lambda$ and the detected intensity; and
determining the position ($x_p$, $y_p$, $z_p$) of the radiation source using the pixel coordinates ($x_i$, $y_i$, $z_i$) and the incidence direction for each of the plurality of pixels.

15. A method of using a pixel detector for determining a position of a divergent radiation source, wherein the pixel detector comprises a detector surface, divided into a plurality of pixels with pixel coordinates ($x_i$, $y_i$, $z_i$), and a detector volume, divided into a plurality of voxels corresponding to the plurality of pixels, wherein each voxel comprises a material with fixed orientation of an internal periodic structure at each of the plurality of voxels;
wherein the using of the pixel detector comprises:
irradiating the pixel detector with radiation originated from the radiation source; wherein the radiation has a predetermined intensity distribution and a wavelength $\lambda$,
detecting an intensity of the incident radiation for each of the plurality of pixels;
determining, for each of the plurality of pixels, an incidence direction of the incident radiation using information on the orientation of the internal periodic structure within the voxel corresponding to the respective pixel and the predetermined intensity distribution, wavelength $\lambda$ and the detected intensity; and
determining the position ($x_p$, $y_p$, $z_p$) of the radiation source using the pixel coordinates ($x_i$, $y_i$, $z_i$) and the incidence direction for each of the plurality of pixels.

16. Method for determining a position of a divergent radiation source, comprising:
irradiating a pixel detector with a predetermined intensity distribution of radiation with wavelength $\lambda$ originated from the radiation source, wherein the pixel detector comprises a plurality of pixels with pixel coordinates ($x_i$, $y_i$, $z_i$);
detecting, for each of the plurality of pixels, an intensity of the incident radiation;
determining, for each of the plurality of pixels, an incidence direction of the incident radiation using information on an orientation of an internal periodic structure of the pixel detector and the predetermined intensity distribution, wavelength $\lambda$ and the detected intensity; and
determining the position ($x_p$, $y_p$, $z_p$) of the radiation source using the pixel coordinates ($x_i$, $y_i$, $z_i$) and the incidence direction for each of the plurality of pixels.

* * * * *